United States Patent [19]

Chiou et al.

[11] Patent Number: 4,521,414

[45] Date of Patent: Jun. 4, 1985

[54] OPHTHALMIC COMPOSITIONS AND THEIR USE FOR TREATING ELEVATED INTRAOCULAR PRESSURE AND GLAUCOMA

[75] Inventors: George C. Y. Chiou, College Station, Tex.; Hsin-Kuang Liu, Boston, Mass.

[73] Assignee: The Texas A&M University System, College Station, Tex.

[21] Appl. No.: 272,889

[22] Filed: Jun. 18, 1981

[51] Int. Cl.³ ............................................. A61K 27/00
[52] U.S. Cl. .................................... 514/229; 514/913
[58] Field of Search .......................... 424/270, 248.51

[56] References Cited

U.S. PATENT DOCUMENTS

| | | | |
|---|---|---|---|
| 3,655,663 | 4/1972 | Wasson | 260/247.1 |
| 3,833,727 | 9/1974 | Nelson et al. | 424/270 |
| 3,891,639 | 6/1975 | Wasson | 424/270 |
| 3,940,407 | 2/1976 | Muchowski et al. | 424/270 |
| 4,097,490 | 6/1978 | Reinhold | 260/326.45 |
| 4,195,085 | 3/1980 | Stone | 424/248.51 |

OTHER PUBLICATIONS

Chem. Abst. 85, 87486(q) (1976)—Katz et al.
"Timoptic"-A.H.F.S. Category 52:36—Aug. 1978–Merck & Co. Inc.
Biochem. Pharm. 30, 103–106, (1981) (Chiou).
Explt. Eye Res (1970) 9, 82–90, Vale et al.
Brit. J. Ophthal (1973) 57,2310, Vale et al.
Kass, M. A. et al., "The Effect of D-isoproterenol on IOP of Rabbit, Monkey, and Man," Inv. Ophthalmol., 15, 113 (1976).
Rowland, J. M. and Potter, D. E., "Adrenergic Drugs and IOP: Effects of D-isomers of Various Agonists", Curr. Eye Res., 1, 25 (1981).
Seidehamel, R. J. et al., "Specific Hypotensive and Antihypertensive Ocular Effects of D-isoproternol in Rabbits", Am. J. Ophthalmol., 79, 1018–1025 (1975).
*Physicians' Desk Reference,* "Timoptic ® Sterile", pp. 1199–1200.
Goodman & Gilman's The Pharmacological Basis of Therapeutics, 6th Ed., Macmillan Publishing Co., Inc., N.Y. 144 (1980).
Meyers, F. H., Jawetz, E. and Goldien, A., Review of Medical Pharmacology, Lange Med. Publishing, Los Altos, CA., 80 (1978).
Drill's Pharmacology in Medicine, McGraw-Hill Book Co., N.Y. 464 (1968).

*Primary Examiner*—Douglas W. Robinson
*Attorney, Agent, or Firm*—Arnold, White & Durkee

[57] ABSTRACT

Antiglaucoma compositions that contain enriched R-(+)-1-tert-butylamino-3-[(4-morpholino-1,2,5-thiadiazol-3-yl)oxy]-2-propanol compared to the S-(−)-isomer and the ophthalmologically acceptable acid addition salts thereof are useful in methods for treating glaucoma and elevated intraocular pressure.

17 Claims, 2 Drawing Figures

OPHTHALMIC COMPOSITIONS AND THEIR USE FOR TREATING ELEVATED INTRAOCULAR PRESSURE AND GLAUCOMA

BACKGROUND OF THE INVENTION

This invention relates to compositions of (R)-(+)-1-tert-butylamino-3-[(4-morpholino-1,2,5-thiadiazol-3-yl)oxy]-2-propanol and ophthalmologically acceptable acid addition salts thereof and their use to lower intraocular pressure, especially in the treatment of ocular hypertension and glaucoma.

Glaucoma is an optic neuropathy associated with elevated intraocular pressures which are too high for normal function and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances have been made in the treatment of glaucoma since pilocarpine and physostigmine were introduced. Recently clinicians have noted that many β-adrenergic blocking agents were effective in reducing intraocular pressure. While many of these were effective in reducing intraocular pressure they also had other characteristics, e.g., membrane stabilizing activity, that were not acceptable for chronic ocular use. S-(−)-1-tert-butylamino-3-[(4-morpholino-1,2,5-thiadiazol-3-yl)oxy]-2-propanol, (timolol), a β-adrenergic blocking agent, was found to reduce intraocular pressure without many of the unwanted side effects associated with pilocarpine and in addition was found to possess advantages over many other β-adrenergic blocking agents, e.g., lack of local anesthesia, long duration of activity, minimal tolerance, etc. It was nevertheless found that S-(−)-1-tert-butylamino-3-[(4-morpholino-1,2,5-thiadiazol-3-yl)oxy]-2-propanol, must be used with caution in those patients that have elevated intraocular pressure and also suffer from bronchial asthma; sinus bradycardia and greater than first degree block; cardiogenic shock; right ventricular failure secondary to pulmonary hypertension; or congestive heart failure; and its concomitant use with adrenergic augmenting cyclotropic drugs must be carefully monitored. These precautions are necessary because even when administered topically to the eye, S-(−)-1-tert-butylamino-3-[(4-morpholino-1,2,5-thiadiazol-3-yl)oxy]-2-propanol is sufficiently active that a small portion is absorbed into the systemic circulation where it can effect other systems.

SUMMARY OF THE INVENTION

The present invention therefore relates to the isomeric form of 1-tert-butylamino-3-[(4-morpholino-1,2,5-thiadiazol-3-yl)oxy]-2-propanol having the R configuration, which, although considerably less active than the S configuration in most other systems outside the eye, nevertheless exhibits in the eye a nearly equivalent degree of activity. This discovery is contrary to the initial belief that in order to achieve full activity in the eye, it was necessary to use the S stereoisomeric form, the form that was most active in other extraocular systems. Indeed, the commercially sold form of 1-tert-butylamino-3-[(4-morpholino-1,2,5-thiadiazol-3-yl)oxy]-2-propanol is the S configuration since this was believed to be the maximally active form. Quite startlingly, the eye has proven to respond differently to the R configuration of timolol than most other extraocular systems. Therefore, to obtain an intraocular pressure reducing response in the eye one does not require that there be employed a composition enriched in S-(−)-1-tert-butylamino-3-[(4-morpholino-1,2,5-thiadiazol-3-yl)oxy]-2-propanol.

This discovery means that in those patients who have a history of asthma or congestive heart disease and for whom (S)-(−)-1-tert-butylamino-3-[(4-morpholino-1,2,5-thiadiazol-3-yl)oxy]-2-propanol was either contraindicated or necessarily prescribed with caution, can now benefit from this revolutionary form of glaucoma therapy. This is because such patients can receive 1-tert-butylamino-3-[(4-morpholino-1,2,5-thiadiazol-3-yl)oxy]-2-propanol enriched in the R isomer with respect to the S isomer or more preferably the R form substantially free of S isomer.

The term "substantially free" as used herein means the isomer indicated is present in greater than 85% purity, and in those instances where resolution techniques permit in greater than 90 or even 95% purity, with respect to other isomers.

The R isomer of 1-tert-butylamino-3-[(4-morpholino-1,2,5-thiadiazol-3-yl)oxy]-2-propanol substantially free of the S isomer is preferably administered in the form of ophthalmic pharmaceutical compositions adapted for topical administration to the eye, such as solutions, ointments or solid inserts. In the cat, a 0.5% solution of R-(+)-3-tert-butylamino-3-[(4-morpholino-1,2,5-thiadiazol-3-yl)oxy]-2-propanol in a normal saline solution was found effective in lowering intraocular pressure. For other species of animal and man, the dose must be adjusted accordingly. Generally, in man the dose must be patient adjusted to employ the minimal dose that reduces intraocular pressure to an acceptable level. In general, formulations of this invention may contain from 0.01 to 5% and especially 0.5 to 2% of medicament. Higher dosages as, for example, about 10% or lower dosages can be employed provided the dose is effective in lowering intraocular pressure. As a unit dosage form between 0.001 to 5.0 mg., preferably 0.005 to 2.0 mg., and especially 0.005 to 1.0 mg. of the compound is generally applied to the human eye.

DESCRIPTION OF THE PREFERRED EMBODIMENTS

Figure 1:
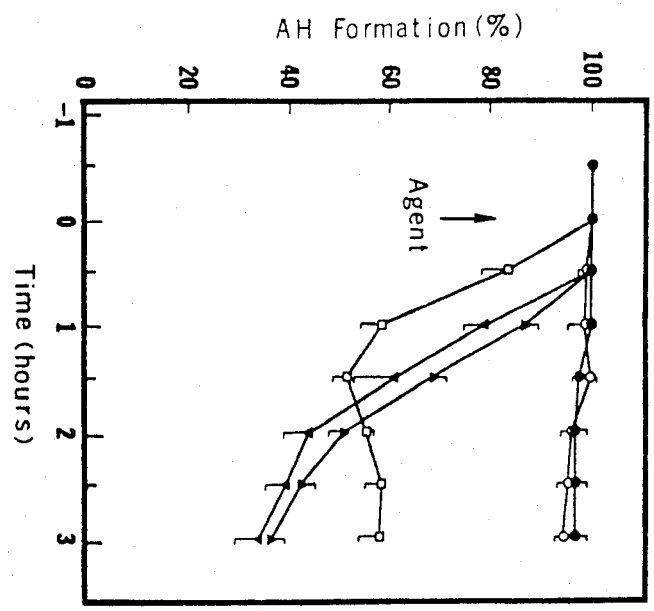
FIG. 1 depicts the time course of percentage change (mean with standard error) of aqueous humor (AH) formation after the administration of ocular hypotensive agents, where (θ), control, (n=3); (o), pilocarpine 0.005% intracamerally, (n=6); (□), acetazolamide 10 mg/Kg i.v. (n=3); (▮), S-(−)-timolol 0.005% intracamerally, (n=3); (▮) R-(+)-timolol 0.005% intracamerally, (n=3).

The efficacy and action mechanism of the R isomer of 1-tert-butylamino-3-[(4-morpholino-1,2,5-thiadiazol-3-yl)oxy]-2-propanol in lowering intraocular pressure were found to be identical to those of the S isomer insofar as the lowering of intraocular pressure is concerned. Table I and FIG. 1 show that the R isomer is as potent as the S isomer to inhibit aqueous humor formation in cat eyes. On the other hand, neither of them affect the rate of aqueous humor outflow (Table II, FIG. 2). The cat model was used for this study because it is superior to the rabbit model which frequently produces false positive results when compared with tests on humans.

such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine oleate, polyoxyethylene sorbitan monopalmi-

TABLE I

EFFECTS OF OCULAR HYPOTENSIVE AGENTS ON AQUEOUS HUMOR (AH) FORMATION

| Agents | N | Rate of AH Formation ($\mu$l/min) | | | | | | | |
|---|---|---|---|---|---|---|---|---|---|
| | | −0.5 hr[§] | 0 hr | 0.5 hr | 1.0 hr | 1.5 hr | 2.0 hr | 2.5 hr | 3.0 hr |
| Control | 3 | 12.1 ± 1.6[π] | 12.1 ± 1.6 | 12.1 ± 1.6 | 12.1 ± 1.6 | 11.8 ± 1.7 | 11.8 ± 1.8 | 11.8 ± 1.8 | 11.8 ± 1.8 |
| Acetazolamide* | 3 | 10.7 ± 1.5 | 10.7 ± 1.5 | 8.9 ± 1.4 | 6.4 ± 1.3 | 5.4 ± 0.6 | 5.9 ± 0.8 | 5.4 ± 1.3 | 6.3 ± 1.3 |
| Pilocarpine[τ] | 6 | 15.2 ± 2.0 | 15.2 ± 5.0 | 15.0 ± 2.0 | 14.7 ± 1.8 | 15.1 ± 1.9 | 14.5 ± 1.8 | 14.3 ± 1.8 | 14.3 ± 1.8 |
| S-(−)-Timolol[γ] | 3 | 11.5 ± 2.3 | 11.5 ± 2.3 | 11.5 ± 2.3 | 9.2 ± 2.0 | 7.2 ± 2.0 | 5.3 ± 1.6 | 4.7 ± 1.4 | 4.0 ± 1.3 |
| R-(+)-Timolol[γ] | 3 | 14.3 ± 1.6 | 14.3 ± 1.6 | 14.3 ± 1.6 | 12.4 ± 1.4 | 9.8 ± 1.1 | 7.2 ± 0.4 | 5.9 ± 0.4 | 5.1 ± 0.3 |

*Acetazolamide 10 mg/kg was given i.v.
[τ]Pilocarpine 0.005% was infused intracamerally.
[γ]Timolol 0.005% was infused intracamerally.
[§]Time before and after drug administration.
[π]Mean ± standard error of the mean.

TABLE II

EFFECTS OF OCULAR HYPOTENSIVE AGENTS ON AQUEOUS HUMOR (AH) OUTFLOW

| Agents | N | Rate of AH outflow ($\mu$l/min) | | | | | | | |
|---|---|---|---|---|---|---|---|---|---|
| | | −0.5 hr[§] | 0 hr | 0.5 hr | 1.0 hr | 1.5 hr | 2.0 hr | 2.5 hr | 3.0 hr |
| Control | 3 | 21.4 ± 1.5[π] | 21.1 ± 1.4 | 22.4 ± 1.4 | 22.7 ± 1.5 | 21.9 ± 0.9 | 22.7 ± 1.7 | 23.6 ± 1.4 | 23.6 ± 1.3 |
| Acetazolamide* | 3 | 19.5 ± 1.4 | 19.8 ± 1.7 | 20.4 ± 1.5 | 19.9 ± 1.6 | 19.9 ± 1.1 | 20.0 ± 1.2 | 20.8 ± 1.1 | 20.8 ± 1.1 |
| Pilocarpine[τ] | 6 | 21.1 ± 2.5 | 21.1 ± 2.4 | 22.4 ± 2.6 | 25.9 ± 2.4 | 31.5 ± 2.9 | 33.2 ± 3.2 | 33.9 ± 3.0 | 34.4 ± 2.6 |
| S-(−)-Timolol[γ] | 3 | 20.6 ± 3.9 | 21.2 ± 4.1 | 21.2 ± 4.5 | 20.7 ± 4.0 | 19.7 ± 3.2 | 20.1 ± 3.7 | 20.0 ± 3.4 | 20.1 ± 3.7 |
| R-(+)-Timolol[γ] | 3 | 21.8 ± 3.3 | 21.8 ± 3.3 | 21.7 ± 3.4 | 21.4 ± 3.3 | 21.1 ± 3.1 | 20.9 ± 3.0 | 21.4 ± 3.6 | 21.5 ± 3.5 |

*, [τ], [γ], [§], [π]See Table I for details.

The invention as hereinbefore stated provides an ophthalmologically active anti-hypertensive agent for the eye, both human and animal, that avoids unwanted effects on extraocular tissues. With the discovery that the R form of 1-tert-butylamino-3-[(4-morpholino-1,2,5-thiadiazol-3-yl)oxy]-2-propanol is active in the eye, and at the same time is relatively inactive, compared to the S isomer, in extraocular tissue, it becomes possible to administer 1-tert-butylamino-3-[(4-morpholino-1,2,5-thiadiazol-3-yl)oxy]-2-propanol that is enriched in the R isomer with respect to the S isomer, and thereby avoid initiation of undesireable extra-ocular effects. Of course, to obtain the maximum freedom from extraocular side reactions R isomer substantially free from S isomer should be administered. Thus, a suitable pharmaceutical dosage is one in which, as compared to 1-tert-butylamino-3-[(4-morpholino-1,2,5-thiadiazol-3-yl)oxy]-2-propanol that is substantially S isomer, the R isomer is enriched with respect to the S isomer.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components tylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert.

While many patients find liquid medication to be entirely satisfactory, others may prefer a solid medicament that is topically applied to the eye, for example, a solid dosage form that is suitable for insertion into the cul-de-sac. To this end the R form of 1-tert-butylamino-3-[(4-morpholino-1,2,5-thiadiazol-3-yl)oxy]-2-propanol can be included with a non-bioerodible insert, i.e., one which after dispensing the drug remains essentially intact, or a bioerodible insert, i.e., one that either is soluble in lacrimal fluids, or otherwise disintegrates. While the insert employed is not critical and those disclosed in Pat. Nos. 3,630,200 Higuchi; 3,811,444 Heller et al.; 4,177,256 Michaels et al.; 3,868,445 Ryde et al.; 3,845,201 Haddad; 3,981,303 Higuchi; and 3,867,519 Michaels, are satisfactory; in general, however, the insert described below is found preferable.

The polymer used to form the preferred insert may be any water soluble non-toxic polymer, for example, cellulose derivatives such as methylcellulose, sodium carboxymethyl cellulose, hydroxyloweralkyl cellulose such as, hydroxyethyl cellulose, hydroxypropyl cellulose, or hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, neutralized carbopol and xanthan gum, and mixtures of said polymers.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert is available in several polymeric forms, all of which are suitable in the preparation of these inserts. Thus, the product sold by Hercules, Inc. of Wilmington, Del. under the name KLUCEL such as KLUCEL HF, HWF, MF, GF, JF, LF and EF which are intended for food or pharmaceutical use are particularly useful. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX a polymer supplied by Union Carbide Co. may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly up to about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50,000 to 100,000; and CARBOPOL (carboxyvinyl polymer) of B. F. Goodrich and Co. designated as grades 934, 940 and 941. It is clear that for the purpose of this invention the type and molecular weight of the polymer is not critical. Any water soluble polymers can be used having an average molecular weight which will afford dissolution of the polymer and accordingly the medicament in any desired length of time. The inserts, therefore, can be prepared to allow for retention and accordingly effectiveness in the eye for any desired period.

The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively, the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye. The insert can be of any suitable size readily fit into the eye. For example, castings or compression molded films having a thickness of about 0.25 mm. to 15.0 mm. can be subdivided to obtain suitable inserts. Rectangular segments of the cast or compressed film having a thickness between about 0.5 and 1.5 mm. can be cut to afford shapes such as rectangular plates of 4×5-20 mm. or ovals of comparable size. Similarly, extruded rods having a diameter between about 0.5 and 1.5 mm. can be cut into suitable sections to provide the desired amount of polymer. For example, rods of 1.0 to 1.5 mm. in diameter and about 20 mm. long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the term smooth and sharp edges or corners are subjective terms, in this application these terms used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di- and tripropylene glycol, hydroxyproply sucrose and the like. Typically, such plasticizers can be present in the ophthalmic insert in an amount ranging from up to about 30% by weight. A particularly preferred plasticizer is water which is present in amounts of at least about 5% up to 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmecuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7-8; usually up to about 2% by weight of polymer. The insert may contain from about 1 mg. to 100 mg. of water soluble polymer, more particularly from 5 to 50 mg. and especially from 5 to 20 mg. The medicament is present from about 0.1 to about 25% by weight of insert.

The hydrogen maleate compound has been studied with respect to its ability to lower aqueous humor formation and intraocular pressure of normal cats and cats with experimental ocular hypertension. This study demonstrated that the compound is very effective in decreasing aqueous humor formation and consequently the intraocular pressure after topical and intracameral application.

EXAMPLE 1

A. Preparation of R,S-1-t-butylamino-2,3,dihydroxypropane

A solution of R,S-glycidol (105 g; 1.42 moles) in 100 ml of isopropanol is added dropwise over one hour to a solution of t-butylamine (197 g; 2.7 moles) in 200 ml isopropanol while maintaining the temperature between 46°–70° C. The solution is aged at 70° C. for one hour and the excess t-butylamine is recovered by atmospheric distillation. The distillation is continued until the pot temperature reaches 110° C. Acetone (700 ml) is then added to the residue and the temperature of the final solution adjusted to 40°–45° C.

B. Resolution of R,S-1-t-butylamino-2,3-dihydroxypropane

To the final solution from (A) is added 83.0 g (0.645 moles) of R-pyroglutamic acid (97% pure) and the resultant solution mixture is refluxed, with stirring, for 1.5 hours. This solution is then cooled to room temperature over 2.5 hours, with stirring.

The R-pyroglutamic acid.R-1-t-butylamino-2,3-dihydroxypropane diastereoisomer which separates from the solution is filtered off and washed with 2×50 ml of acetone.

C. Regeneration of R-1-t-butylamine-2,3-dihydroxypropane

The R-1-t-butylamino-2,3-dihydroxypropane is regenerated from the (B) diastereoisomer by dissolving the diastereoisomer in 200 ml of water and passing the solution through a column of 350 ml of IR-120 (H+). IR-120 (H+) is a gelular, strongly acidic, cation exchange resin marketed by Rohn & Haas Company. The column is washed with water until a negative test for pyroglutamic acid is obtained. R-pyroglutamic acid was recovered, in excess of 95% yield, by concentrating to dryness, slurrying the residue with isopropanol and filtering off the R-pyroglutamic acid.

The R-1-t-butylamino-2,3-dihydroxypropane is eluted from the IR-120 resin by washing with 5% ammonium hydroxide solution. The eluate is concentrated to dryness and the residue recrystallized from 150 ml of xylene to give pure R-1-t-butylamino-2,3-dihydroxypropane, (R(+)-glycolamine).

EXAMPLE 2

Step A. Preparation of R-2-phenyl-3-tert-butyl-5-hydroxymethyloxazolidine

A mixture of R(+)-glycolamine (20 g.; 0.136 mole), benzaldehyde (50 ml.; 288 mmole) and benzene (30 ml.) is heated under reflux for 8 hours while removing the water as formed into a Dean Stark trap filled with benzene. The temperature of the reaction mixture is maintained at 110°–113° C. over the entire period. The benzene is removed in vacuo (15 mm. pressure) and the excess benzaldehyde is removed by distillation at 0.1 mm. pressure. The residual oil R-2-phenyl-3-tert-butyl-5-hydroxymethyloxazoline can be used directly in the next step. If desired, the oxazolidine can be distilled to provide a product of higher purity.

Step B. Preparation of R-(+)-3-morpholino-4-(3-tert-butylamino-2-hydroxypropoxy)-1,2,5-thiadiazole and its hydrogen maleate salt A mixture of 3-morpholino-4-chloro-1,2,5-thiadiazole (2.05 g.; 10 mmole), R-2-phenyl-3-tert-butyl-5-hydroxymethyl oxazolidine (10 mmole) and potassium tert-butoxide in tert-butanol (11.7 ml. of 0.885 N, 10 mmole) is stirred at 25° C. for 16 hours. The solvent then is evaporated in vacuo and the residue treated with 20 ml. of 1 N hydrochloric acid. The mixture is heated at 65° C. for one-half hour, cooled to 25° C. and extracted with ether. The aqueous layer is made alkaline with potassium carbonate and extracted with ether. The extracts are washed with water, dried and evaporated to an oily residue of R-(+)-3-morpholino-4-(3-tert-butylamino-2-hydroxypropoxy)-1,2,5-thiadiazole. This oil is dissolved in 50 ml. of tetrahydrofuran, treated with charcoal (1.5 g.), filtered, and the cake washed with 20 ml. of tetrahydrofuran. To this solution is added maleic acid [5.0 g.; 1 mole equivalent per mole of R-(+)-3-morpholino-4-(3-tertbutylamino 2-hydroxypropoxy)-1,2,5-thiadiazol] dissolved in tetrahydrofuran (25 ml.). The mixture then is seeded and aged one hour at 25° C. The crystallized hydrogen maleate salt is separated by filtration, washed with tetrahydrofuran and dried at 50° C. in vacuo to give R-(+)-3-morpholino-4-(3-tert-butylamino-2-hydroxypropoxy)-1,2,5-thiadiazol hydrogen maleate.

By replacing the maleic acid employed in the above procedure by hydrochloric acid, sulfuric acid, tartaric acid or any other desired acid the corresponding acid salt is formed.

EXAMPLE 3

| Solution Composition | A | B |
|---|---|---|
| R—(+)-1-tert-butylamino-3-[(4-morpholino-1,2,5-thiadiazol-3-yl)oxy]-2-propanyl hydrogen maleate (I) | 1 mg. | 15 mg. |
| Sodium phosphate monobasic .2H$_2$O | 9.38 mg. | 6.10 mg. |
| Dibasic sodium phosphate .12H$_2$O | 28.48 mg. | 16.80 mg. |
| Benzalkonium chloride | 0.10 mg. | 0.10 mg. |
| Sodium hydroxide q.s. | pH 6.8 | pH 6.8 |
| Water for injection q.s. ad. | 1.0 ml. | 1.0 ml. |

(I), phosphate buffer salts, and benzalkonium chloride are added to and dissolved in water. The pH of the solution is adjusted to 6.8 with sodium hydroxide and the final solution diluted to volume. The solution is rendered sterile by filtration through a sterilizing filter.

EXAMPLE 4

| | |
|---|---|
| R—(+)-1-tert-butylamino-3-[(4-morpholino-1,2,5-thiadiazol-3-yl)oxy]-2-propanol hydrogen maleate (I) | 5 mg. |
| petrolatum q.s. ad. | 1 gram |

Compound (I) and the petrolatum are aseptically combined.

EXAMPLE 5

| | |
|---|---|
| R—(+)-1-tert-butylamino-3-[(4-morpholino-1,2,5-thiadiazol-3-yl)oxy]-2-propanol hydrogen maleate (I) | 1 mg. |
| Hydroxypropyl cellulose q.s. | 12 mg. |

Ophthalmic inserts are manufactured from compression molded films which are prepared on a Carver Press by subjecting the powder mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 6

| | |
|---|---|
| R—(+)-1-tert-butylamino-3-[(4-morpholino-1,2,5-thiadiazol-3-yl)oxy]-2-propanyl hydrogen maleate (I) | 1 mg. |
| Hydroxypropyl cellulose q.s. ad. | 12 mg. |

Ophthalmic inserts are manufactured from a solvent cast film prepared by making a viscous solution of the powder mixture of the above ingredients using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 7

| | |
|---|---|
| R—(+)-1-tert-butylamino-3-[(4-morpholino-1,2,5-thiadiazol-3-yl)oxy]-2-propanyl hydrogen maleate (I) | 1 mg. |
| Hydroxypropyl methyl cellulose q.s. ad. | 12 mg. |

Ophthalmic inserts are manufactured from a solvent cast film which is prepared by making a viscous solution of the powder blend of the above ingredients using a methanol/water solvent system (10 ml. methanol is added to 2.5 g. of powder blend, to which 11 ml. of water (in three divided portions) is added). The solution is placed on a Teflon plate and allowed to dry at ambient conditions. After drying, the film is placed in an 88% R. H. cabinet until it is pliable. Appropriately sized inserts are then cut from the film.

Other ophthalmologically acceptable salt forms of 1-tert-butylamino-3-[(4-morpholino-1,2,5-thiadiazol-3-yl)oxy]-2-propanol enriched in the R isomer with respect to the S can be employed in the above examples in place of R-(+)-1-tert-butylamino-3-[(4-morpholino-1,2,5-thiadiazol-3-yl)oxy]-2-propanyl hydrogen maleate.

Ophthalmic inserts are manufactured from compression molded films which are prepared on a Carver Press by subjecting the powder mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and so as insure against recontamination, the sterilization is preferably conducted after packaging. The best mode of sterilizing is to employ ionizing irradiation including irradiation emanating from Cobalt 60 or high energy electron beams.

After packaging a convenient quantity of inserts, usually a single dose, the package is exposed to a sterilizing quantity of radiation. The preferred packaging employs sealing the inserts between layers of film or foil and then sealing or laminating the layers together about the edges. The techniques for performing the sterilization are well known and accepted, for example, as outlined in International Atomic Energy Commission, *Code of Practice for Radiosterilization of Medical Products*, 1967, pp. 423–431; and *Block, Disinfection, Sterilization and Preservation*, 2nd Ed., Lea & Febiger, Philadelphia, 1977, pp. 542–561.

The required quantity of irradiation can be determined experimentally by testing irradiated inserts for viable bacteria. Generally, the amount of irradiation desired to achieve sterilization is defined by the $D_{10}$ value. The $D_{10}$ value is the radiation dose that will reduce a given population of organisms by a factor of 10. Based on $D_{10}$ values, experimentally obtained for *Bacillus pumilus*, and presterilization contamination levels, a dose of 1.36 megarads is effective in obtaining a sterile product.

EXAMPLE 8

This example shows the efficacy of R-(+)-1-tert-butylamino-3-[(4-morpholino-1,2,5-thiadiazol-3-yl)oxy]-2-propanol in inhibiting aqueous humor formation and consequently the intraocular pressure on a newly developed cat model. The cat model was developed for continuous, simultaneous, and instant display of aqueous humor dynamics with a microspectrophotometer and a sensitive drop counter. This method allows a precise prediction of a drug's ability to lower intraocular pressure in human patients. It is superior to the rabbit model because the latter frequently gives false positive results and is therefore a poor method for screening the ocular hypotensive activity of β-adrenergic antagonists.

Cats were anesthetized with 30 mg/kg of pentobarbital. The head was stabilized with a stereotoxic head holder. Three 25-gauge needle infusion sets were placed through the cornea into the eye. One was placed in the anterior chamber for the detection of intraocular pressure. The second needle was placed in the posterior chamber for the infusion of perfusate. The third one was placed in the anterior chamber for the overflow of aqueous humor solution which passed through a microspectrophotometric cell for detection of blue dextran concentration and a sensitive drop counter for measurement of aqueous humor solution overflow rate. Drugs were given intracamerally through the second needle or topically.

Figure 2:
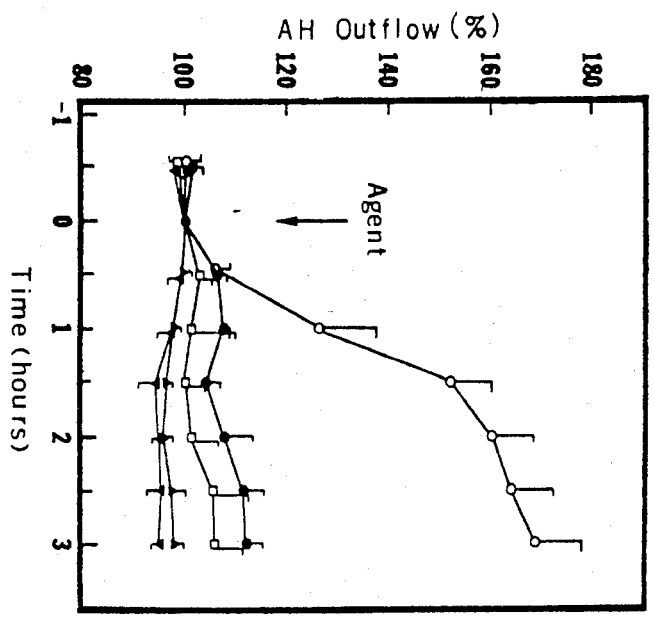
FIG. 2 depicts the time course of percentage change (mean with standard error) of aqueous humor (AH) outflow after the administration of ocular hypotensive agents (see description of FIG. 1 for legend in detail).

The method was verified with pilocarpine which increases aqueous humor outflow (FIG. 2, Table II) without affecting the aqueous humor formation (FIG. 1, Table I). The reverse was true with acetazolamide and the S-(−)-isomer of timolol (FIGS. 1 and 2, Table I and II). It is important to note that the aqueous humor formation was inhibited while aqueous humor outflow was unaffected by both the R-(+) isomer and S-(−) isomer of timolol. These results indicate that the R-(+) isomer of timolol acts identically to its S-(−)-isomer in the eyes. This discovery is of great importance since the R-(+)-timolol is ineffective in blocking β-adrenergic receptors in the extraocular tissues and thus does not produce untoward side effects.

The foregoing description has been directed to particular embodiments of the invention in accordance with the requirements of the Patent Statutes for the purposes of illustration and explanation. It will be apparent however, to those skilled in this art that many modifications and changes in the apparatus and procedure set forth will be possible without departing from the scope and spirit of the invention. It is applicant's invention that the following claims be interpreted to embrace all such modifications and variations.

What is claimed is:

1. A method of reducing aqueous humor formation and intraocular pressure in mammals having ocular hypertension which comprises topically administering to a hypertensive eye an ophthalmologically acceptable amount, effective for lowering intraocular pressure, of a compound selected from R-(+)-1-tert-butylamino-3-[(4-morpholino-1,2,5-thiadiazol-3-yl)oxy]-2-propanol and ophthalmologically acceptable acid addition salts thereof.

2. A method according to claim 1 wherein the compound is in the form of a water-soluble ophthalmologically acceptable salt and is applied topically in an aqueous solution containing between 0.01% to about 5% of said compound.

3. A method according to claim 1 wherein the compound is in the form of a water-soluble ophthalmologically acceptable salt and is applied topically in an aqueous solution containing between 0.5% to about 2% of said compound.

4. A method according to claim 1 wherein the compound is R-(+)-1-tert-butylamino-3-[(4-morpholino-1,2,5-thiadiazol-3-yl)oxy]-2-propanol.

5. A method according to claims 1, 2 or 3 wherein the compound is R-(+)-1-tert-butylamino-3-[(4-morpholino-1,2,5-thiadiazol-3-yl)oxy]-2-propanyl hydrogen maleate.

6. A method according to claim 1 wherein the compound is topically applied in the form of an ointment.

7. A method according to claim 1 wherein said compound is topically applied by an ophthalmologically acceptable polymeric ocular insert placed and retained in contact with the eyeball, said compound being diffusible from said insert at a rate sufficient to provide an ophthalmologically acceptable, effective intraocular pressure lowering dose thereof to the eye when said insert is in contact therewith.

8. An ophthalmic composition for the topical treatment of glaucoma comprising in solution an intraocular pressure lowering effective amount of a water-soluble ophthalmologically acceptable acid addition salt of R-(+)-1-tert-butylamino-3-[(4-morpholino-1,2,5-thiadiazol-3-yl)oxy]-2-propanol and a liquid ophthalmic carrier.

9. An ophthalmic composition according to claim 8 wherein said acid addition salt is R-(+)-1-tert-butylamino-3-[(4-morpholino-1,2,5-thiadiazol-3-yl)oxy]-2-propanyl hydrogen maleate.

10. An ophthalmic composition according to claim 9 wherein the solution comprises from about 0.01% to about 5% by weight R-(+)-1-tert-butylamino-3-[(4-morpholino-1,2,5-thiadiazol-3-yl)oxy]-2-propanyl hydrogen maleate.

11. An ophthalmic composition according to claim 9 wherein the solution comprises from about 0.5% to about 2% by weight R-(+)-1-tert-butylamino-3-[(4-morpholine-1,2,5-thiadiazol-3-yl)oxy]-2-propanyl hydrogen maleate.

12. A pharmaceutical unit dosage form for the topical treatment of glaucoma comprising about 0.001 mgs. to about 5.0 mgs. of R-(+)-1-tert-butylamino-3-[(4-morpholino-1,2,5-thiadiazol-3-yl)oxy]-2-propanyl hydrogen maleate in an isotonic aqueous solution.

13. A pharmaceutical unit dosage form according to claim 12 wherein the amount of R-(+)-1-tert-butylamino-3-[(4-morpholino-1,2,5-thiadiazol-3-yl)oxy]-2-propanyl hydrogen maleate is from about 0.005 mgs. to about 2.0 mgs.

14. A method according to claim 1 wherein the compound is administered in a water soluble polymeric insert.

15. A method according to claim 14 wherein the polymer is hydroxypropyl cellulose.

16. A method for treating glaucoma and for lowering intraocular pressure which comprises topically applying to an affected eye an intraocular pressure lowering amount of R-(+)-1-tert-butylamino-3-[(4-morpholino 1,2,5-thiadiazol-3-yl)oxy]-2-propanol or an opthalmologically acceptable acid addition salt thereof.

17. An ophthalmic composition for the topical treatment of glaucoma and ocular hypertension comprising from about 0.01% to 5% by weight of R-(+)-1-tert-butylamino-3-[(4-morpholino-1,2,5-thiadiazol-3-yl)oxy]-2-propanol or an ophthalmologically acceptable acid addition salt thereof and an ophthalmic acceptable topical carrier.

* * * * *